United States Patent
Wang et al.

(10) Patent No.: US 6,515,118 B1
(45) Date of Patent: Feb. 4, 2003

(54) DNA FRAGMENTATION FACTOR

(75) Inventors: Xiaodong Wang, Dallas, TX (US); Xuesong Liu, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 08/842,760

(22) Filed: Apr. 17, 1997

(51) Int. Cl.[7] .......................... C07H 21/02; C12N 1/20; C12N 15/00; C12N 5/02
(52) U.S. Cl. ................. 536/23.1; 435/69 T; 435/520.1; 435/325
(58) Field of Search .......................... 536/23.1; 435/325, 435/320.1, 69 T

(56) References Cited

U.S. PATENT DOCUMENTS 4,889,806 A * 12/1989 Olson et al. ............. 435/172.3
5,731,185 A * 3/1998 Meda et al. ................ 435/194
5,948,888 A * 9/1999 De La Monte et al. ..... 530/350

OTHER PUBLICATIONS

The World of Pharmacia, Pharmacia Biotech, Uppsala, Sweden, p. 115, 1995.*
Burgess et al (J. Cell Biol, 111: 2129–2138), 1990.*
Lazar et al (Mol. Cell. Biol., 8: 1247–1252), 1988.*
Tao (J. Immunol, 143: 2595–2601), 1989.*
Gibbs et a (Biochemistry, 26: 1332–1343), 1987.*
Ruffner et al (Mol. Biol. Evol., 4:1–9), 1987*
Chissoe et al (Genomics, 27: 67–82), 1995.*
Sambrook et al (Molecular Cloning, A Laboratory, 1989.* Manual, 2nd Ed. Cold Spring Harbor Press, Cold Spring Harbor p. 16. 3–16.4*
Lehninger et al (Principles of Biochemistry, 2nd Ed., Worth Publishers, NY, p. 335), 1993.*
Hillier et al (T89792, Genbank Sequence Database (Accession T8972), National Center for Biotechnology Information, National Library of Medicine, Bethesday, MD), 1995.*
Sambrook et al (Molecular Cloning, A Laboratory Manual, 2nd Ed., Cold Spring Harbor Press, Cold Spring Harbor, p. 16.3–16.4), 1989.*
Marra et al (G1752630), Genbank Sequence Database (Accession AA171314), National Center for Biotechnology Information, National Livrary of Medicine, Bethesda, Maryland, 1996.*
Yupsanis et al (J.Plant Physiology, 149:641–649), 1994.*

* cited by examiner

*Primary Examiner*—Anthony C. Caputa
(74) *Attorney, Agent, or Firm*—Richard Aron Osman

(57) ABSTRACT

The invention provides methods and compositions relating to DNA Fragmentation Factor (DFF) polypeptides and related nucleic acids. The polypeptides may be produced recombinantly from transformed host cells from the disclosed DFF encoding nucleic acids or purified from human cells. The invention provides isolated DFF hybridization probes and primers capable of specifically hybridizing with the disclosed DFF genes, DFF-specific binding agents such as specific antibodies, and methods of making and using the subject compositions in diagnosis, therapy and in the biopharmaceutical industry.

18 Claims, No Drawings

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
      (A) LENGTH: 1689 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 113..1105

(xi) SEQUENCE DESCRIPTION: SEQ ID NO: 1:

```
GCGTCGACCG AACTACATCT CCCGGCAGGC TGCGGAAGGG GGTCGAGTAG AAGGACCGCC        60

GCTCCGGCCT CCCGCGACTT CTCGAAGGTG GGCAGGTCCC ACCTTGTGGA GG ATG          115
                                                         Met
                                                           1

GAG GTG ACC GGG GAC GCC GGG GTA CCA GAA TCT GGC GAG ATC CGG ACT        163
Glu Val Thr Gly Asp Ala Gly Val Pro Glu Ser Gly Glu Ile Arg Thr
            5                  10                  15

CTA AAG CCG TGT CTG CTG CGC CGC AAC TAC AGC CGC GAA CAG CAC GGC        211
Leu Lys Pro Cys Leu Leu Arg Arg Asn Tyr Ser Arg Glu Gln His Gly
         20                  25                  30

GTG GCC GCC TCC TGC CTC GAA GAC CTG AGG AGC AAG GCC TGT GAC ATT        259
Val Ala Ala Ser Cys Leu Glu Asp Leu Arg Ser Lys Ala Cys Asp Ile
 35                  40                  45

CTG GCC ATT GAT AAG TCC CTG ACA CCA GTC ACC CTT GTC CTG GCA GAG        307
Leu Ala Ile Asp Lys Ser Leu Thr Pro Val Thr Leu Val Leu Ala Glu
 50                  55                  60                  65

GAT GGC ACC ATA GTG GAT GAT GAC GAT TAC TTT CTG TGT CTA CCT TCC        355
Asp Gly Thr Ile Val Asp Asp Asp Asp Tyr Phe Leu Cys Leu Pro Ser
             70                  75                  80

AAT ACT AAG TTT GTG GCA TTG GCT AGT AAT GAG AAA TGG GCA TAC AAC        403
Asn Thr Lys Phe Val Ala Leu Ala Ser Asn Glu Lys Trp Ala Tyr Asn
```

|  |  |  |  |  |  |  |  |  |  |  |  |  |  |  |  |
|---|---|---|---|---|---|---|---|---|---|---|---|---|---|---|---|
|  |  |  | 85 |  |  |  | 90 |  |  |  | 95 |  |  |  |  |
| AAT | TCA | GAT | GGA | GGT | ACA | GCT | TGG | ATT | TCC | CAA | GAG | TCC | TTT | GAT | GTA | 451 |
| Asn | Ser | Asp | Gly | Gly | Thr | Ala | Trp | Ile | Ser | Gln | Glu | Ser | Phe | Asp | Val |  |
|  |  |  | 100 |  |  |  | 105 |  |  |  | 110 |  |  |  |  |
| GAT | GAA | ACA | GAC | AGC | GGG | GCA | GGG | TTG | AAG | TGG | AAG | AAT | GTG | GCC | AGG | 499 |
| Asp | Glu | Thr | Asp | Ser | Gly | Ala | Gly | Leu | Lys | Trp | Lys | Asn | Val | Ala | Arg |  |
|  | 115 |  |  |  | 120 |  |  |  | 125 |  |  |  |  |  |  |
| CAG | CTG | AAA | GAA | GAT | CTG | TCC | AGC | ATC | ATC | CTC | CTA | TCA | GAG | GAG | GAC | 547 |
| Gln | Leu | Lys | Glu | Asp | Leu | Ser | Ser | Ile | Ile | Leu | Leu | Ser | Glu | Glu | Asp |  |
| 130 |  |  |  |  | 135 |  |  |  | 140 |  |  |  |  | 145 |  |  |
| CTC | CAG | ATG | CTT | GTT | GAC | GCT | CCC | TGC | TCA | GAC | CTG | GCT | CAG | GAA | CTA | 595 |
| Leu | Gln | Met | Leu | Val | Asp | Ala | Pro | Cys | Ser | Asp | Leu | Ala | Gln | Glu | Leu |  |
|  |  |  | 150 |  |  |  | 155 |  |  |  | 160 |  |  |  |  |
| CGT | CAG | AGT | TGT | GCC | ACC | GTC | CAG | CGG | CTG | CAG | CAC | ACA | CTC | CAA | CAG | 643 |
| Arg | Gln | Ser | Cys | Ala | Thr | Val | Gln | Arg | Leu | Gln | His | Thr | Leu | Gln | Gln |  |
|  |  |  | 165 |  |  |  | 170 |  |  |  | 175 |  |  |  |  |
| GTG | CTT | GAC | CAA | AGA | GAG | GAA | GTG | CGT | CAG | TCC | AAG | CAG | CTC | CTG | CAG | 691 |
| Val | Leu | Asp | Gln | Arg | Glu | Glu | Val | Arg | Gln | Ser | Lys | Gln | Leu | Leu | Gln |  |
|  |  |  | 180 |  |  |  | 185 |  |  |  | 190 |  |  |  |  |
| CTG | TAC | CTC | CAG | GCT | TTG | GAG | AAA | GAG | GGC | AGC | CTC | TTG | TCA | AAG | CAG | 739 |
| Leu | Tyr | Leu | Gln | Ala | Leu | Glu | Lys | Glu | Gly | Ser | Leu | Leu | Ser | Lys | Gln |  |
|  | 195 |  |  |  | 200 |  |  |  | 205 |  |  |  |  |  |  |
| GAA | GAG | TCC | AAA | GCT | GCC | TTT | GGT | GAG | GAG | GTG | GAT | GCA | GTA | GAC | ACG | 787 |
| Glu | Glu | Ser | Lys | Ala | Ala | Phe | Gly | Glu | Glu | Val | Asp | Ala | Val | Asp | Thr |  |
| 210 |  |  |  |  | 215 |  |  |  | 220 |  |  |  |  | 225 |  |  |
| GGT | ATC | AGC | AGA | GAG | ACC | TCC | TCG | GAC | GTT | GCG | CTG | GCG | AGC | CAC | ATC | 835 |
| Gly | Ile | Ser | Arg | Glu | Thr | Ser | Ser | Asp | Val | Ala | Leu | Ala | Ser | His | Ile |  |
|  |  |  | 230 |  |  |  | 235 |  |  |  | 240 |  |  |  |  |
| CTT | ACT | GCA | CTG | AGG | GAG | AAG | CAG | GCT | CCA | GAG | CTG | AGC | TTA | TCT | AGT | 883 |
| Leu | Thr | Ala | Leu | Arg | Glu | Lys | Gln | Ala | Pro | Glu | Leu | Ser | Leu | Ser | Ser |  |
|  |  |  | 245 |  |  |  | 250 |  |  |  | 255 |  |  |  |  |
| CAG | GAT | TTG | GAG | TTG | GTT | ACC | AAG | GAA | GAC | CCC | AAA | GCA | CTG | GCT | GTT | 931 |
| Gln | Asp | Leu | Glu | Leu | Val | Thr | Lys | Glu | Asp | Pro | Lys | Ala | Leu | Ala | Val |  |
|  |  |  | 260 |  |  |  | 265 |  |  |  | 270 |  |  |  |  |
| GCC | TTG | AAC | TGG | GAC | ATA | AAG | AAG | ACG | GAG | ACT | GTT | CAG | GAG | GCC | TGT | 979 |
| Ala | Leu | Asn | Trp | Asp | Ile | Lys | Lys | Thr | Glu | Thr | Val | Gln | Glu | Ala | Cys |  |
|  | 275 |  |  |  | 280 |  |  |  | 285 |  |  |  |  |  |  |
| GAG | CGG | GAG | CTC | GCC | CTG | CGC | CTG | CAG | CAG | ACG | CAG | AGC | TTG | CAT | TCT | 1027 |
| Glu | Arg | Glu | Leu | Ala | Leu | Arg | Leu | Gln | Gln | Thr | Gln | Ser | Leu | His | Ser |  |
| 290 |  |  |  |  | 295 |  |  |  | 300 |  |  |  |  | 305 |  |  |
| CTC | CGG | AGC | ATC | TCA | GCA | AGC | AAG | GCC | TCA | CCA | CCT | GGT | GAC | CTG | CAG | 1075 |
| Leu | Arg | Ser | Ile | Ser | Ala | Ser | Lys | Ala | Ser | Pro | Pro | Gly | Asp | Leu | Gln |  |
|  |  |  | 310 |  |  |  | 315 |  |  |  | 320 |  |  |  |  |
| AAT | CCT | AAG | CGA | GCC | AGA | CAG | GAT | CCC | ACA | TAGCAGCAGC | GGGAAGTGTG |  |  |  |  | 1125 |
| Asn | Pro | Lys | Arg | Ala | Arg | Gln | Asp | Pro | Thr |  |  |  |  |  |  |  |
|  |  |  | 325 |  |  |  | 330 |  |  |  |  |  |  |  |  |

```
CCAAGGAAGC TCTGTGGCGT TGTGTTATTG GTAGACACCC TCAGCCTCAT CATTTGACTA    1185

CCTATGTACT ACTCTACCCC CTGCCTTAGA GCACCTTCCA GAGAAGCTAT TCCAGGTCTC    1245

AACATACGCC GTTCCACCAA TTTTTTTTTT AGCCCCACCA GCTTCAGGAC TTCTGCCAAT    1305

TTTGAATGAT ATAGCTGCAC CAACAATATC CCGCCTCCTC TAATTACATA TGATGTTCTC    1365

TGTTCAAAAG TAATTGGCAG TGATTGGCCA GGCGCAGTGG CTCACGCCTG TAATCCCAGC    1425

ACTGGGAGGC CGAGGGGGGC GGATCGTGAA GTCAGGAGAT CGAGACCATC CTGGCTAACA    1485

TGGTGAAACC CTGTCTCTAC TAAAAATACA AAAAAAATTA GCCAGCCATG GTGGCGGGCG    1545

CCTGTAATCC CAGCTACTTG GGAGGCTGAG GCAGGAGAAT GGCATGAACC TGGGAGGCAG    1605

AGCTTGCAGT GAGCTGAGAT TGCGCCACTG CACTCCAGCC TGGGCAACAG AGCGAGACTC    1665
```

CGTCTCAAAA AAAAAAAAAA AAAA                                                     1689

(2) INFORMATION FOR SEQ ID NO: 2:

(i) SEQUENCE CHARACTERISTICS:
        (A) LENGTH: 331 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Glu Val Thr Gly Asp Ala Gly Val Pro Glu Ser Gly Glu Ile Arg
 1               5                  10                  15

Thr Leu Lys Pro Cys Leu Leu Arg Arg Asn Tyr Ser Arg Glu Gln His
             20                  25                  30

Gly Val Ala Ala Ser Cys Leu Glu Asp Leu Arg Ser Lys Ala Cys Asp
         35                  40                  45

Ile Leu Ala Ile Asp Lys Ser Leu Thr Pro Val Thr Leu Val Leu Ala
     50                  55                  60

Glu Asp Gly Thr Ile Val Asp Asp Asp Tyr Phe Leu Cys Leu Pro
 65                  70                  75                  80

Ser Asn Thr Lys Phe Val Ala Leu Ala Ser Asn Glu Lys Trp Ala Tyr
             85                  90                  95

Asn Asn Ser Asp Gly Gly Thr Ala Trp Ile Ser Gln Glu Ser Phe Asp
            100                 105                 110

Val Asp Glu Thr Asp Ser Gly Ala Gly Leu Lys Trp Lys Asn Val Ala
            115                 120                 125

Arg Gln Leu Lys Glu Asp Leu Ser Ser Ile Ile Leu Leu Ser Glu Glu
130                 135                 140

Asp Leu Gln Met Leu Val Asp Ala Pro Cys Ser Asp Leu Ala Gln Glu
145                 150                 155                 160

Leu Arg Gln Ser Cys Ala Thr Val Gln Arg Leu Gln His Thr Leu Gln
                165                 170                 175

Gln Val Leu Asp Gln Arg Glu Glu Val Arg Gln Ser Lys Gln Leu Leu
            180                 185                 190

Gln Leu Tyr Leu Gln Ala Leu Glu Lys Glu Gly Ser Leu Leu Ser Lys
        195                 200                 205

Gln Glu Glu Ser Lys Ala Ala Phe Gly Glu Glu Val Asp Ala Val Asp
    210                 215                 220

Thr Gly Ile Ser Arg Glu Thr Ser Ser Asp Val Ala Leu Ala Ser His
225                 230                 235                 240

Ile Leu Thr Ala Leu Arg Glu Lys Gln Ala Pro Glu Leu Ser Leu Ser
                245                 250                 255

Ser Gln Asp Leu Glu Leu Val Thr Lys Glu Asp Pro Lys Ala Leu Ala
            260                 265                 270

Val Ala Leu Asn Trp Asp Ile Lys Lys Thr Glu Thr Val Gln Glu Ala
        275                 280                 285

Cys Glu Arg Glu Leu Ala Leu Arg Leu Gln Gln Thr Gln Ser Leu His
    290                 295                 300

Ser Leu Arg Ser Ile Ser Ala Ser Lys Ala Ser Pro Pro Gly Asp Leu
305                 310                 315                 320

Gln Asn Pro Lys Arg Ala Arg Gln Asp Pro Thr
                325                 330
```

```
(2) INFORMATION FOR SEQ ID NO: 3:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO: 3:

Asp Glu Val Asp
1

(2) INFORMATION FOR SEQ ID NO: 4:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO: 4:

Asp Glu Pro Asp
1

(2) INFORMATION FOR SEQ ID NO: 5:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO: 5:

Tyr Val Ala Asp
1

(2) INFORMATION FOR SEQ ID NO: 6:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO: 6:

Asp Glu Ala Asp
1
```

DNA FRAGMENTATION FACTOR

FIELD OF THE INVENTION

The field of this invention is proteins involved in chromatin destabilization.

BACKGROUND

Apoptosis is executed through a suicide program that is built into all animal cells (reviewed by White,1996; Wyllie, 1995). Cells undergoing apoptosis show distinctive morphological changes, including membrane blebbing, cytoplasmic and nuclear condensation, chromation aggregation and formation of apoptotic bodies (Wyllie, 1980). The biochemical hallmark of apoptosis is the cleavage of chromatin into nucleosomal fragments (Wyllie et al., 1980). Multiple lines of evidence indicate that apoptosis can be triggered by the activation of a family of cysteine proteases with specificity for aspartic acid residues, including CED-3 of C. elegans, CPP32/Yama/Apopain of humans, and DCP-1 of Drosophila (Yuan et al., 1993; Xue et al., 1996; Fernandes-Alnemri, et al., 1994; Tewari, et al., 1995; Nicholson, et al., 1995; Song, et al., 1997). Recently, these proteins have been designated as caspases (Alnemri et al., 1996).

The most intensively studied apoptotic caspase is caspase-3, previously called CPP32/Yama/Apopain (Fernandes-Alnemri, et al., 1994; Tewari, et al., 1995; Nicholson, et al., 1995). Caspase-3 normally exists in the cytosolic fraction of cells as an inactive precursor that is activated proteolytically when cells are signaled to undergo apoptosis (Schlegel et al., 1996; Wang et al., 1996). Multiple apoptotic signals, including serum withdrawal, activation of Fas, treatment with granzyme B, ionizing radiation, and a variety of pharmacological agents, activate caspase-3 (Chinnaiyan et al., 1996; Darmon, et al., 1996; Datta et al., 1996, 1997; Erhardt and Cooper, 1996; Hasegawa et al., 1996; Jacobson et al., 1996; Martin et al., 1996; Schlegel et al, 1996). A caspase-3-specific tetrapeptide inhibitor, Ac-DEVD SEQ ID NO:3-CHO, can abolish the ability of cytosol from apoptotic cells to induce apoptosis in normal nuclei and block the initiation of the cellular apoptotic program in response to apoptotic stimuli (Nicholson et al., 1995; Dubrez, et al., 1996; Jacobson et al., 1996). Deletion of caspase-3 from the mouse genome through homologous recombination results in excessive accumulation of neuronal cells, owing to a lack of apoptosis in the brain (Kuida et al., 1996). Addition of active caspase-3 to normal cytosol activates the apoptotic program (Enari et al., 1996). These data indicate that caspase-3 is both necessary and sufficient to trigger apoptosis.

The identified substrates of caspase-3 include poly(ADP-ribose) polymerase (PARP) (Tewari et al. 1995; Nicholson et al., 1995), sterol-regulatory element binding proteins (SREBPs) (Wang et al., 1995; 1996), the U1 associated 70 kDa protein (Caciola-Rosen et al. 1996), D4-GDI (Na et al., 1996), huntingtin (Goldberg et al., 1996), and the DNA-dependent protein kinase (Casciola-Rosen et al., 1996; Song et al., 1996). It is not known whether the cleavage of any of these substrates plays a causal role in apoptosis.

Our laboratory recently established an experimental system in which DNA fragmentation characteristic of apoptosis can be triggered in vitro by incubation of normal nuclei with activated cytosolic extracts (Liu et al., 1996b). The activation occurred in two stages: first, cytosolic caspase-3 was cleaved and activated in a reaction that was triggered by cytochrome c released from mitochondria; and second, activated caspase-3 interacted with other cytosolic components to generate DNA fragmentation when added to isolated nuclei (Liu et al., 1996b; Yang et al., 1997). The present invention describes the purification, characterization, and cDNA cloning of a downstream factor that is activated by caspase-3 and in turn induces nuclear DNA fragmentation. We call this factor DNA Fragmentation Factor (DFF).

SUMMARY OF THE INVENTION

The invention provides methods and compositions relating to isolated DNA Fragmentation Factor (DFF) polypeptides, related nucleic acids, and polypeptide domains thereof having DFF-specific activity. DFF polypeptides can regulate chromatin stability and hence provide important regulators of cell viability. The polypeptides may be produced recombinantly from transformed host cells from the subject DFF encoding nucleic acids or purified from mammalian cells. The invention provides isolated DFF hybridization probes and primers capable of specifically hybridizing with the disclosed DFF gene, DFF-specific binding agents such as specific antibodies, and methods of making and using the subject compositions in diagnosis (e.g. genetic hybridization screens for DFF transcripts), therapy (e.g. gene therapy to modulate DFF gene expression) and in the biopharmaceutical industry (e.g. as immunogens, reagents for isolating other transcriptional regulators, reagents for screening chemical libraries for lead pharmacological agents, etc.).

DETAILED DESCRIPTION OF THE INVENTION

The DNA Fragmentation Factor (DFF) polypeptides of the invention include DFF-45, DFF-40, and polypeptides comprising domains thereof. Such DFF domains have at least 10, preferably at least about 12, more preferably at least about 14 consecutive residues of DFF-45 or DFF-40 and provide DFF domain specific activity or function, such as being a caspase-3 substrate, mediating DNA fragmentation, activating a nuclease and inhibiting a DFF polypeptide.

The nucleotide sequence of a natural cDNA encoding a human DFF-45 polypeptide is shown as SEQ ID NO:1, and the full conceptual translate is shown as SEQ ID NO:2. The DFF polypeptides of the invention include incomplete translates of SEQ ID NO:1 and deletion mutants of SEQ ID NO:2, which translates and deletion mutants have DFF-specific amino acid sequence and binding specificity or function.

DFF-specific activity or function may be determined by convenient in vitro, cell-based, or in vivo assays: e.g. in vitro binding assays, cell culture assays, in animals (e.g. gene therapy, transgenics, etc.), etc. Binding assays encompass any assay where the molecular interaction of an DFF polypeptide with a binding target is evaluated. The binding target may be a natural intracellular binding target such as another DFF polypeptide, a DFF regulating protein, a DFF-activated nuclease, or other regulator that directly modulates DFF activity or its localization; or non-natural binding target such a specific immune protein such as an antibody, or an DFF specific agent such as those identified in screening assays such as described below. DFF-binding specificity may assayed by binding equilibrium constants (usually at least about $10^7$ $M^{-1}$, preferably at least about $10^8$ $M^{-1}$, more preferably at least about $10^9$ $M^{-1}$), by the ability of the subject polypeptide to function as negative mutants in DFF-expressing cells, to elicit DFF specific antibody in a heterologous host (e.g a rodent or rabbit), etc. In any event, the DFF binding specificity of the subject DFF polypeptides necessarily distinguishes AIF.

The claimed DFF polypeptides are isolated or pure: an "isolated" polypeptide is unaccompanied by at least some of the material with which it is associated in its natural state, preferably constituting at least about 0.5%, and more preferably at least about 5% by weight of the total polypeptide in a given sample and a pure polypeptide constitutes at least about 90%, and preferably at least about 99% by weight of the total polypeptide in a given sample. The DFF polypeptides and polypeptide domains may be synthesized, produced by recombinant technology, or purified from mammalian, preferably human cells. A wide variety of molecular and biochemical methods are available for biochemical synthesis, molecular expression and purification of the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, NY) or that are otherwise known in the art.

The invention provides natural and non-natural DFF-specific binding agents, methods of identifying and making such agents, and their use in diagnosis, therapy and pharmaceutical development. For example, in addition to functions disclosed below, chromatin stability may be dependent on the stability of certain DFF complexes and is subject to regulation by modulating the stability of the DFF complex. Hence, agents which modulate the stability of DFF complexes such as DFF-45/DFF-40 provide means for regulating cell growth and viability. Such agents have the advantage of bypassing many mechanisms of MDR frequently associated with neoproliferative disease. Novel DFF-specific binding agents include DFF-specific receptors, such as somatically recombined polypeptide receptors like specific antibodies or T-cell antigen receptors (see, e.g Harlow and Lane (1988) Antibodies, A Laboratory Manual, Cold Spring Harbor Laboratory) and other natural intracellular binding agents identified with assays such as one-, two- and three-hybrid screens, non-natural intracellular binding agents identified in screens of chemical libraries such as described below, etc. For diagnostic uses, the binding agents are frequently labeled, such as with fluorescent, radioactive, chemiluminescent, or other easily detectable molecules, either conjugated directly to the binding agent or conjugated to a probe specific for the binding agent. Agents of particular interest modulate DFF function, e.g. DFF-dependent apoptosis; for example, isolated cells, whole tissues, or individuals may be treated with an DFF binding agent to activate, inhibit, or alter DFF-dependent apoptotic processes.

The amino acid sequences of the disclosed DFF polypeptides are used to back-translate DFF polypeptide-encoding nucleic acids optimized for selected expression systems (Holler et al. (1993) Gene 136, 323–328; Martin et. al. (1995) Gene 154, 150–166) or used to generate degenerate oligonucleotide primers and probes for use in the isolation of natural DFF-encoding nucleic acid sequences ("GCG" software, Genetics Computer Group, Inc, Madison Wis.). DFF-encoding nucleic acids used in DFF-expression vectors and incorporated into recombinant host cells, e.g. for expression and screening, transgenic animals, e.g. for functional studies such as the efficacy of candidate drugs for disease associated with DFF-modulated cell viability, etc.

The invention also provides nucleic acid hybridization probes and replication/amplification primers having a DFF cDNA specific sequence contained in SEQ ID NO:1 and sufficient to effect specific hybridization thereto (i.e. specifically hybridize with SEQ ID NO:1 in the presence of HeLa cell cDNA). Such primers or probes are at least 12, preferably at least 24, more preferably at least 36 and most preferably at least 96 bases in length. Demonstrating specific hybridization generally requires stringent conditions, for example, hybridizing in a buffer comprising 30% formamide in 5×SSPE (0.18 M NaCl, 0.01 M NaPO$_4$, pH7.7, 0.001 M EDTA) buffer at a temperature of 42° C. and remaining bound when subject to washing at 42° C. with 0.2×SSPE; preferably hybridizing in a buffer comprising 50% formamide in 5×SSPE buffer at a temperature of 42° C. and remaining bound when subject to washing at 42° C. with 0.2×SSPE buffer at 42° C. DFF cDNA homologs can also be distinguished from other polypeptide using alignment algorithms, such as BLASTX (Altschul et al. (1990) Basic Local Alignment Search Tool, J Mol Biol 215, 403–410).

The subject nucleic acids are of synthetic/non-natural sequences and/or are isolated, i.e. unaccompanied by at least some of the material with which it is associated in its natural state, preferably constituting at least about 0.5%, preferably at least about 5% by weight of total nucleic acid present in a given fraction, and usually recombinant, meaning they comprise a non-natural sequence or a natural sequence joined to nucleotide(s) other than that which it is joined to on a natural chromosome. Nucleic acids comprising the nucleotide sequence of SEQ ID NO:1 or fragments thereof, contain such sequence or fragment at a terminus, immediately flanked by a sequence other than that which it is joined to on a natural chromosome, or flanked by a native flanking region fewer than 10 kb, preferably fewer than 2 kb, which is at a terminus or is immediately flanked by a sequence other than that which it is joined to on a natural chromosome. While the nucleic acids are usually RNA or DNA, it is often advantageous to use nucleic acids comprising other bases or nucleotide analogs to provide modified stability, etc.

The subject nucleic acids find a wide variety of applications including use as translatable transcripts, hybridization probes, PCR primers, diagnostic nucleic acids, etc.; use in detecting the presence of DFF genes and gene transcripts and in detecting or amplifying nucleic acids encoding additional DFF homologs and structural analogs. In diagnosis, DFF hybridization probes find use in identifying wild-type and mutant DFF alleles in clinical and laboratory samples. Mutant alleles are used to generate allele-specific oligonucleotide (ASO) probes for high-throughput clinical diagnoses. In therapy, therapeutic DFF nucleic acids are used to modulate cellular expression or intracellular concentration or availability of active DFF.

The invention provides efficient methods of identifying agents, compounds or lead compounds for agents active at the level of a DFF modulatable cellular function. Generally, these screening methods involve assaying for compounds which modulate DFF interaction with a natural DFF binding target. A wide variety of assays for binding agents are provided including labeled in vitro protein-protein binding assays, immunoassays, cell based assays, etc. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development.

In vitro binding assays employ a mixture of components including an DFF polypeptide, which may be part of a fusion product with another peptide or polypeptide, e.g. a tag for detection or anchoring, etc. The assay mixtures comprise a natural intracellular DFF binding target. While native binding targets may be used, it is frequently preferred to use portions (e.g. peptides) thereof so long as the portion provides binding affinity and avidity to the subject DFF polypeptide conveniently measurable in the assay. The assay mixture also comprises a candidate pharmacological agent. Candidate agents encompass numerous chemical classes, though typically they are organic compounds; preferably small organic compounds and are obtained from a wide variety of sources including libraries of synthetic or natural compounds. A variety of other reagents may also be included in the mixture. These include reagents like salts, buffers, neutral proteins, e.g. albumin, detergents, protease inhibitors, nuclease inhibitors, antimicrobial agents, etc. may be used.

The resultant mixture is incubated under conditions whereby, but for the presence of the candidate pharmacological agent, the DFF polypeptide specifically binds the cellular binding target, portion or analog with a reference binding affinity. The mixture components can be added in any order that provides for the requisite bindings and incubations may be performed at any temperature which facilitates optimal binding. Incubation periods are likewise selected for optimal binding but also minimized to facilitate rapid, high-throughput screening.

After incubation, the agent-biased binding between the DFF polypeptide and one or more binding targets is detected by any convenient way. For cell-free binding type assays, a separation step is often used to separate bound from unbound components. Separation may be effected by precipitation (e.g. TCA precipitation, immunoprecipitation, etc.), immobilization (e.g on a solid substrate), etc., followed by washing by, for examples, membrane filtration, gel chromatography (e.g. gel filtration, affinity, etc.). For cell-based DFF-dependent DNA fragmentation, 'binding' is detected by a change in the chromatin stability of the cell.

Detection may be effected in any convenient way. For cell-free binding assays, one of the components usually comprises or is coupled to a label. The label may provide for direct detection as radioactivity, luminescence, optical or electron density, etc. or indirect detection such as an epitope tag, an enzyme, etc. A variety of methods may be used to detect the label depending on the nature of the label and other assay components, e.g. through optical or electron density, radiative emissions, nonradiative energy transfers, etc. or indirectly detected with antibody conjugates, etc.

A difference in the binding affinity of the DFF polypeptide to the target in the absence of the agent as compared with the binding affinity in the presence of the agent indicates that the agent modulates the binding of the DFF polypeptide to the DFF binding target. Analogously, in the cell-based assay also described below, a difference in the DFF-dependent chromatin degredation or instability in the presence and absence of an agent indicates the agent modulates DFF function. A difference, as used herein, is statistically significant and preferably represents at least a 50%, more preferably at least a 90% difference.

The following experimental section and examples are offered by way of illustration and not by way of limitation.

EXPERIMENTAL

Identification of DFF

To elucidate the molecular events leading to DNA fragmentation, we set up an in vitro DNA fragmentation assay in which normal nuclei from hamster liver were incubated with active recombinant caspase-3 together with Hela cell S-100 cytosol. Caspase-3 alone was not able to induce DNA fragmentation in the co-incubated nuclei; neither were the HeLa cell cytosolic or nuclear extracts. However, when caspase-3 and the HeLa S-100 fraction were incubated togather with the nuclei, DNA fragmentation occurred. These data indicate the existence of a DNA fragmentation factor(s) (DFF) in HeLa cell cytosol which induces DNA fragmentation in the presence of caspase-3. No DFF activity was detected in the nuclear extract.

Purification of DFF

Using caspase-3-dependent DNA fragmentation as an assay, we purified DFF from HeLa cell S-100 in an eight-step procedure (Table 1 and Methods and Materials).

TABLE 1

Purification of DFF from HeLa cells

| Step | Fraction | Protein mg | Specific Activity units/mg | Total Activity unit | Purification -fold | Recovery % |
|---|---|---|---|---|---|---|
| 1 | S-100 | 3750 | 526 | 1972500 | | 100 |
| 2 | SP-Sepharose | 968 | 1466 | 1419355 | 2.8 | 72 |
| 3 | Phenyl-Sepharose | 275 | 3040 | 835820 | 5.8 | 42 |
| 4 | 50% Ammonium-Sulfate Precipitation | 88 | 8333 | 733333 | 16 | 37 |
| 5 | Superdex-200 | 20 | 34285 | 685714 | 65 | 35 |
| 6 | MonoS | 0.675 | 227920 | 153846 | 433 | 7.8 |
| 7 | Hydroxyapatite | 0.2 | 328947 | 65789 | 625 | 3.3 |
| 8 | MonoQ | 0.015 | 4000000 | 60000 | 7604 | 3.0 |

S-100 was purified from 100 liters of HeLa cells as described in Experimental Procedures. An aliquot of each fraction was dialyzed against buffer A and the DFF activity was assayed at five concentrations of protein. The results were quantified by IS-1000 Digital Imaging System(Alpha Innotech Corporation). One unit of activity was arbitrarily defined as one unit of intensity of the single nucleosomal DNA.

DFF activity eluted from a Mono Q column, the last step of the purification, at about 250 mM NaCl. These fractions were subjected to SDS-PAGE followed by Coomassie Brilliant Blue staining. Two polypeptides with molecular masses of 45 kDa and 40 kDa were observed to co-elute with the DFF activity. We used the Coomassie stain because the 45 kDa protein stained poorly with silver. No other proteins were detected in fraction containing the peak of DFF activity.

Purified DFF from the Mono Q column induced DNA fragmentation in co-incubated nuclei in a fashion that was dependent on its concentration and the concentration of caspase-3. As increasing amounts of purified DFF were added to the reaction, the extent of DNA fragmentation increased as demonstrated by the increase in the intensity of small size nucleosomal DNA fragments (~180 base pair/nucleosome) and the decrease of large molecular weight genomic DNA. At the highest concentration used, almost all the DNA was cleaved into the size of single nucleosomes after 2 hr. No DNA fragmentation was observed when caspase-3 was omitted from the reaction. A similar pattern, although not as linear, was observed when increasing amounts of caspase-3 were added to the reactions with a fixed amount of DFF. Interestingly, DFF plus caspase-3 showed no detectable nuclease activity when incubated with naked DNA.

The relative linear increase in single nucleosomal fragments in response to increasing concentrations of DFF enabled us to quantitatively estimate the degree of purification of DFF. Table 1 shows estimates of the quantitative parameters for the purification of DFF starting with S-100 fraction from 100 liters of suspension cultured HeLa cells. The DFF was purified more than 7,000-fold to apparent homogeneity through the Mono Q step with an overall recovery of 3% activity.

To confirm the association of the 45-kDa and 40-kDa polypeptides, we applied the purified DFF from the Mono Q column step to a Superdex-200 gel-filtration column (Pharmacia). The column fractions were collected and assayed for DFF activity. DFF activity appeared at fractions 8 and 9 with an estimated molecular mass of 85 kDa relative to the molecular weight standard. The same fractions were also subjected to SDS-PAGE followed by Coomassie Blue staining and the 45-kDa and 40-kDa polypeptides were observed to co-elute with DFF activity.

Characterization of DFF

Several known substrates of caspase-3 are nuclear proteins, including PARP, lamin B1, 70 kD U1 RNP protein and DNA-dependent kinase. To test the possibility that the function of DFF is to facilitate the transport of caspase-3 into nuclei, we studied the time course of cleavage of lamin B1 by caspase-3 in the absence or presence of DFF, and found that caspase-3 alone was not able to induce DNA fragmentation. In the presence of DFF, nuclear DNA started to fragment after 15 min of incubation and the extent of fragmentation increased with time. However, the rate of Lamin B1 cleavage by caspase-3 remained the same with or without DFF. These data indicate that caspase-3 cuts the nuclear substrate with or without DFF. The same conclusion was obtained when the rate of cleavage of PARP was measured.

DFF Functions Downstream of Caspase-3

We next conducted an experiment to determine whether caspase-3 was needed for DNA fragmentation after it had activated DFF, or whether the sole requirement for caspase-3 is to activate DFF. To distinguish these possibilities we employed a caspase-3 specific tetrapeptide aldehyde inhibitor, Ac-DEAD SEQ ID NO:6-CHO (Wang et al., 1995). Incubation of caspase-3 and DFF together induced DNA fragmentation, while caspase-3 or DFF alone failed to do so. When Ac-DEAD SEQ ID NO:6-CHO was included in the reaction, DNA fragmentation was inhibited, demonstrating that activation of DFF requires active caspase-3. Under the same conditions, the ICE specific inhibitor, Ac-YVAD SEQ ID NO:5-CHO, did not inhibit DNA fragmentation. In contrast, when caspase-3 and DFF were pre-incubated for 2 hr followed by the addition of nuclei and Ac-DEAD SEQ ID NO:6-CHO, there was no longer inhibition of DNA fragmentation reaction. These data indicate that caspase-3 activity is no longer required for DNA fragmentation once DFF is activated.

The above protocol also provided an opportunity to determine whether the cleavage of nuclear substrates by caspase-3, such as PARP and Lamin B1, are necessary for DNA fragmentation. It had not been clear whether the cleavage of PARP or Lamins is a required step for DNA fragmention. To directly test this requirement, we pre-incubated purified DFF with caspase-3 and then added nuclei in the presence of Ac-DEAD SEQ ID NO:6-CHO, or the control inhibitor Ac-YVAD SEQ ID NO:5-CHO. Neither Ac-DEAD SEQ ID NO:6-CHO nor Ac-YVAD SEQ ID NO:5-CHO had any effect on DNA fragmentation when added after DFF and caspase-3 had been pre-incubated. However, Ac-DEAD SEQ ID NO:6-CHO still blocked the cleavage of both PARP and lamin B1 in the co-incubated nuclei. These data indicate that DNA fragmentation does not require cleavage of nuclear substrates such as PARP and lamin B1.

45-kDa Subunit of DFF is a Substrate for Caspase-3

Inasmuch as activation of DFF by caspase-3 is inhibited by Ac-DEAD SEQ ID NO:6-CHO, it is likely that this activation involves the cleavage of one or both of the subunits of DFF. To test this hypothesis, we labeled purified DFF with biotin and incubated the biotinylated DFF with caspase-3. After incubation, the samples were subjected to SDS-PAGE and visualized by chemiluminescence using streptavidin-conjugated peroxidase. Both subunits of DFF were labeled with biotin. Incubation with caspase-3 resulted in the cleavage of the 45-kDa subunit into fragments of molecular masses of 30 kDa and 11 kDa that were separated by SDS-PAGE; the 40-kDa subunit remained intact.

To confirm that DFF-45 is cleaved and activated in vivo in cells undergoing apoptosis, we performed immuno-blot analysis of DFF-45 using extracts from human monocytic U937 cells undergoing apoptosis induced by staurosporine and found that DFF-45 exists as ~45-kDa precursor in growing cells. After a 2 hr treatment with staurosporine, DFF-45 was cleaved into fragments of 30 and 11 kDa. At later time points the 30-kDa fragment was reduced and the 11-kDa increased. The cleavage of DFF-45 into fragments of 30 and 11 kDa has also been observed in other cell types such as HeLa cells and human fibroblast SV589. Similar results were obtained when U937 cells were induced to undergo apoptosis with etoposide. The data suggest that there are multiple caspase-3 cleavage sites in DFF45. The 30-kDa fragment is an intermediate that is further cleaved to an 11 kDa form. The time of appearance of the 11-kDa fragments correlated well with the fragmentation of chromatin in these U937 cells.

Protein sequencing analysis of DFF-45 and DFF-40 (data from 4 tryptic peptides ranging from 7 to 16 amino acids, 50 amino acids total) revealed that both are previously uncharacterized proteins. We isolated a cDNA clone encoding the 45-kDa subunit based on the protein sequence generated from tryptic digestion of DFF-45 followed by Edman degradation. The cDNA contains an open reading frame of 331 amino acids with no obvious homology with any known proteins in the data base. The translated product of this eDNA in a rabbit reticulocyte lysate runs at the identical position as purified DFF-45 in SDS-PAGE.

To map the caspase-3 cleavage sites in DFF-45, we expressed the protein with a six-histidine tag at the $NH_2$-terminus. The fusion protein migrates at about 45 kDa on SDS-PAGE after purification on a nickel affinity column. Incubation of this fusion protein with caspase-3 resulted in its cleavage into three fragments of 30 kDa, 18 kDa and 11 kDa at the early time point, and the 30 kDa fragment was further cleaved into ~11 kDa fragments with longer incubation. These fragments were separated by SDS-PAGE and electroblotted onto Immobilon Psq for automated Edman degradation. The results revealed that the $NH_2$-terminal residues of the fragments were Gly-2 (30 and 18 kDa), Ser-138 (11 kDa), and Thr-245 (11 kDa) respectively, suggesting that caspase-3 had cleaved between Asp-137 and Ser-138 and between Asp-244 and Thr-245. This generates two different fragments of ~11 kDa that could not be separated on SDS-PAGE. The 18 kDa fragment is probably generated as the result of His-tag at the $NH_2$-terminal of the fusion protein, which runs at ~11 kDa if it was from the native DFF-45.

To confirm that these are the principal sites of cleavage, unfractionated samples of digested DFF-45 were subjected to electrospray mass spectrometry. This analysis revealed protein fragments of mass 23,732, 14,833, 12,036 and 11,713 Da. These values corresponded with those calculated for the peptide expected from the results of Edman degradation, namely Ser-138 to Thr-351 (23,736), Gly-2 to Asp-137 (14,836), Ser-138 to Asp-244 (12,039) and Thr-245 to Thr-351 (11,715) The $NH_2$-terminal fragment of DFF-45 runs slowly on SDS-PAGE. The $NH_2$-terminal sequence analysis and the mass spectrometry of the cleavage products revealed that cleavage occurs at the sequence DETD SEQ ID NO:2, residue 114–117 (a.a. 117) and DAVD SEQ ID NO:2, residues 221–224 (a.a. 224). These cleavage sites are consistent with the known cleavage sites for caspase-3 such as DEVD SEQ ID NO:3 for PARP and DEPD SEQ ID NO:4 for SREBP-2 (Nicholson et al., 1995; Wang et al., 1995). These data delineate a direct signal transduction pathway during apoptosis: caspase-3 to DFF to DNA fragmentation.

General Methods and Materials

We obtained Ac-Tyr-Val-Ala-Asp SEQ ID NO:5-aldehyde (Ac-YVAD-CHO) Biochem & Bioscience Inc.; Ac-Asp-Glu-Ala-Asp SEQ ID NO:6-aldehyde (Ac-DEAD-CHO) as described in (Wang et al, 1995); Protease K and DNase free RNase A from Worthington; Commasie Brilliant Blue, Molecular weight standards for SDS-PAGE and gel filtration chromatography from Bio-Rad; Protein concentrations were determined by the Bradford method; General molecular biology methods were as in Sambrook et al. HeLa cell cytosol was prepared as described (Liu et al., 1996b).

Assay for DNA Fragmentation Factor (DFF)

Caspase-3 was prepared as described in (Liu et al., 1996a). The purified enzyme was stored in Buffer A (20 mM Hepes-KOH, pH 7.5, 10 mM KCL, 1.5 mM MgCl, 1 mM sodium EDTA, 1 mM sodium EGTA, 1 mM DTT, and 0.1 mM PMSF) containing 20% glycerol and 1 mg/ml bovine serum albumin (BSA) in multiple aliquots at −80° C. Hamster liver nuclei were prepared as described in (Liu et al., 1996b); HeLa cell nuclei and nuclear extract were prepared as in (Wang et al., 1993). Purified nuclei were resuspended in buffer B (10 mM PIPES, pH 7.4, 80 mM KCl, 20 mM NaCl, 5 mM sodium EGTA, 250 mM sucrose, and 1 mM DTT) at $8.5 \times 10^7$ nuclei/ml and stored in multiple aliquots at −80° C. The DNA fragmentation was assayed by incubating an aliquot (7 ml) of hamster liver or HeLa cell nuclei and 6 ml of caspase-3 with the indicated enzyme fractions at 37° C. for 2 hr in a final volume of 60 ml adjusted with buffer A. After incubation, 330 ml of buffer C (100 mM Tris-HCl, pH 8.5, 5 mM EDTA, 0.2 M NaCl, 0.2% w/v SDS, and 0.2 mg/ml proteinase K) was added to each reaction and incubated at 37° C. overnight. NaCl was then added to a final concentration of 1.5 M and the nuclear debris was spun down for 15 min in a microcentrifuge at room temperature. The DNA in the supernatants were precipitated with equal volume of 100% ethanol. The DNA precipitate was washed once with 70% (v/v) ethanol and resuspented in 40 ml of buffer D (10 mM Tris-HCl, pH 7.5, 1 mM sodium EDTA and 200 mg/ml DNase-free RNase A). After incubation at 37° C. for 2 hr, the DNA was loaded onto a 2% agarose gel and electrophoresis was conducted at 50 V for 2 hr in 0.5×Tris-Borate-EDTA (TBE) buffer (1×TBE buffer contains 90 mM Tris-Borate/2 mM EDTA). The gel was stained with 2 mg/ml ethidium bromide for 15 min, destained with water for 1 hr, and visualized under UV light.

Purification of DFF from HeLa S-100

All purification steps were carried out at 4° C. All chromatography steps except the SP-Sepharose column and the phenyl-Sepharose column were carried out using an automatic fast protein liquid chromatography (FPLC) station (Pharmacia)

750 ml of HeLa S-100 from 100 liter of suspension cultured HeLa cells were applied to a SP-Sepharose column (200 ml bed volume) equilibrated with buffer A. The column was washed with three column volumes of buffer A and eluted with two column volumes of buffer A containing 0.5 mM NaCl. Ammonium sulfate (1 M) was added directly to the Sp-Sepharose 0.5 M eluate. After rotating at 4° C. for 1 hr, the sample were centrifuged at 15,000 rpm for 30 min in a Sovall JA-600 rotor. The supernatant was directly loaded onto a 100 ml phenyl sepharose column equilibrated with buffer A containing 1 M ammonium sulfate and 0.5 M NaCl. The column was washed with three bed volumes of buffer A containing 1 M ammonium sulfate and 0.5 M NaCl and the bound material was eluted with two bed volumes of buffer A. Ammonium sulfate was added to the phenyl sepharose eluate to 50% saturation. After stirring at 4° C. for 5 hr, the sample was centrifuged at 15,000 rpm for 15 min in a Sovall JA-600 rotor. The pellet was resuspended in buffer A and loaded onto a Superdex-200 16/60 gel filtration column (Pharmacia) equilibrated with buffer A and eluted with the same bufer. Fractions of 4 ml were collected and assayed for DFF activity. The active fractions from the gelfiltration column were pooled and loaded onto a MonoS 10/10 column (Pharmacia) equilibrated with buffer A. The column was washed with 50 ml of buffer A and eluted with a 200 ml 0–0.2 M linear NaCl gradient. Fractions of 4 ml were collected and assayed for DFF activity. The active fractions from the MonoS column were pooled and loaded onto a 1 ml hydroxyapatite column (Bio-Rad) equilibrated with buffer A. The column was washed with 10 ml of buffer A and the bound material was eluted with 0–0.25 M linear phosphate gradient. 1 ml fractions were collected and assayed for DFF activity. The active fractions was pooled and loaded onto a Mono Q 5/5 column (Pharmacia) equilibrated with buffer A. The column was washed with 10 ml of buffer A containing 0.1 M NaCl and DFF was eluted from the column with a 30 ml 0.1–0.3 M linear NaCl gradient. Fractions of 1 ml were collected and assayed for DFF activity.

Western Blot Analysis

A monoclonal antibody against human PARP (c-2-10) was used as described in (Kauftmann et al, 1993). A monoclonal antibody against human lamin B1 was from Calbiochem. Anti-DFF-45 anti-serum was generated by immunizing rabbits with a recombinant DFF-45 fusion protein (see below). Immunoblot analysis was performed with the horseradish peroxidase conjugated goat anti-mouse (PARP and lamin B1) or goat anti-rabbit (DFF-45) immunoglobulin G using Enhanced Chemiluminescence western blotting detection reagents (Amersham).

Biotinylation of DFF

The biotinylation of DFF was carried out using a ECL protein biotinylation kit (Amersham) with modifications.

Briefly, 0.6 mg of purified DFF was incubated with 10 ml of biotinylation reagent in 120 ml of 40 mM bicarbonate buffer at room temperature for 1 hr. Then 20 ml of 1 M Tris-HCl (pH 8.0) was added to the reaction followed by incubation at room temperature for 1 hr. The sample was then dialyzed against buffer F (20 mM Tris-HCl, PH 7.5, 10 mM Kcl. 1.5 mM MgCl2, 1 mM sodium EDTA, 1 mM sodium DGTA, 1 mM DTT, 1 mM PMSF) at 4° C. overnight.

cDNA Cloning of DFF45

Hela poly(A)+ mRNA was purified using Rapid mRNA Purification kit (Pharmacia). First-strand cDNA synthesis was carried out using a First Strand cDNA Synthesis kit with oligo(dT) primers (Pharmacia). The cDNA was amplified with 40 pmol oligonucleotides designed from an EST clone (#116412) that encodes one of the DFF45 peptide sequence. A 395 bp PCR product was subcloned into the PCR II vector using the TA cloning kit (Invitrogen) and sequenced. The 395 bp PCR product was subsequently labeled with [$^{32}$P] dCTP using redi prime RANDOM Primer Labelling kit (Amersham) and used to screen a Hela 1 gt11 cDNA library by hybridizing duplicate filter at 42° C. for 3 hr in Rapid-hyb buffer (Amersham). The filters were washed twice wither 1×saline citrate (SSC)/0.1% SDS for 15 min at room temperature and once with 0.5×SSC/0.1% SDS for 10 min at 65° C. Out of 8×10$^5$ plaques screened, a 1.3 kb partial length clone was identified and subcloned into the EcoRI site of PCRII vector (In Vitro Gene). A 1.0 kb EcoRI/BamHI fragment was excised from 5' end of the 1.3 kb insert and labeled with dCTP as described above. A Hela 1 Exlox library (Yokoyama et al., 1993) was screened with this 1 kb cDNA fragment as described above. In 6×10$^5$ plaques screened, 30 positive clones were identified. A 1.6 kb clone which contains the longest open reading frame was sequenced in both strands in an automated sequencer.

Production of DFF-45 Fusing Protein

Primers were designed to PCR-amplify the DFF-45 cDNA open reading frame and the amplified cDNA was subcloned inframe into the NdeI/XhoI sites of the bacterial expression vector pET-15b (Novagen). The expression plasmid was transformed into bacteria BL21(DE3). In a typical DFF-45 preparation, a 10 ml overnight cultured bacteria containing DFF-45 expression vector was added into a 500 ml LB broth, cultured for 3 hr by shaking at 220 rpm in 37° C., and then isopropyl-1-thio-B-D-galactopyranoside (IPTG) was added to a final concentration of 1 mM and cultured for another 2 hr. The bacterial pellet was resuspended in 10 ml of buffer A and broken by sonication. After centrifugation at 4,000 g for 15 min, the supernatant was loaded onto a nickel affinity column (6 ml). The column was washed with 30 ml buffer A containing 1 M NaCl followed by 20 ml of Buffer A. The column was eluted with Buffer A containing 250 mM imidazole. About 10 mg DFF-45 protein was purified from a 500 ml culture.

REFERENCES

Alnemri, E. S., et al. (1996). Cell 87, 171.
Armstrong, R. C., et al. (1996). J. Biol. Chem. 271, 16850–168555.
Boldin, M. P., et al. (1996). Cell 85, 803–815.
Boulakia, C. A., et al. (1996). Oncogene. 12, 529–535.
Caciola-Rosen, L., et al. (1996). J. Exp. Med. 183, 1957–1964.
Chinnaiyan, A. M., et al. (1996). J. Biol. Chem. 271, 4573–4576.
Darmon, A. J., et al. (1996). J. Biol. Chem. 271, 21709–21712.
Datta, R., et al. (1996). Blood. 88, 1936–1943.
Datta, R., et al. (1997). J. Biol. Chem. 272, 1965–1969.
Dubrez, L., et al. (1996). EMBO, J. 15, 5504–5512.
Enari, M., et al. (1996). Nature 380, 723–726.
Erhardt, P., and Cooper, G. M. (1996). J. Biol. Chem. 271,17601–17604.
Fernandes-Alnemri, T. G., et al. (1994). J. Biol. Chem. 269, 30761–30764.
Gaido, M. L., and Cidlowski, J. A. (1991). J. Biol. Chem. 266, 18580–18585.
Goldberg, Y. P., et al. (1996) Nat. Genet. 13(4), 442–449.
Hasegawa, J., et al. (1996). Cancer Res. 56, 1713–1718.
Ibrado, A. M., et al.(1996). Cancer Res. 56, 4743–4748.
Jacobson, M. D., et al. 1996). J. Cell. Biol. 133, 1041–1051.
Kauftmann, S. H., et al. (1993) Cancer Res. 53, 3976–3985.
Kluck, R. M., et al. (1997) Science 275, 1132–1136.
Kuida K., et al. (1996). Nature 384, 368–372.
Liu, X., et al.(1996a) J. Biol. Chem. 271, 13371–13376.
Liu, X., et al.(1996b) Cell 86, 147–157.
Martin, S. J., et al. (1996). EMBO J. 15, 2407–2416.
McConkey, D. J. (1996). J. Biol. Chem. 271, 22398–22406.
Monney, L., et al. (1996). Biochem. Biophy. Res. Comm. 221, 340–345.
Muzio, M., et al. (1996). Cell 85, 817–827.
Muzio, M., et al.(1997). Biol. Chem. 272, 2952–2956.
Na, S., et al. (1996). J. Biol. Chem. 271, 11209–11213.
Nicholson, W. D., et al. (1995) Nature 376, 37–43.
Nikonova, L. V., et al. (1993). Eur. J. Biochem. 215, 893–901.
Peitsch, M. C., et al. (1993). EMBO J. 12, 371–377.
Quan, L. T., et al. (1996). Proc. Nat. Acad. Sci. USA. 93, 1972–1976.
Sambrook, J., et al. (1989). Mol. Cloning A Lab. Manual, 2nd ed, Cold Spring Harbor Lab Press.
Schlegel, J., et al. (1996). J. Biol. Chem. 271, 1841–1844.
Song, Q., et al. (1996). EMBO, J. 15, 3238–3246.
Song, Z., et al. (1997). Science 275, 536–540.
Susin, S. A., et al. (1996). J. Exp. Med. 184, 1331–1341.
Tewari, M., et al. (1995). Cell 81, 801–809.
Wang, Z-Q., et al. (1995). Gene & Dev. 9, 509–520.
Wang, X., et al. (1993). J. Biol. Chem. 268, 14497–14504
Wang, X., et al. (1995). J. Biol. Chem. 270, 18044–18050.
Wang, X., et al. (1996). EMBO J. 15, 1012–1020.
White, E. (1996). Genes & Dev. 10, 1–15.
Wyllie, A. H. (1980). Nature 284, 555–556.
Wyllie, A. H. (1995). Curr. Opin. in Gen. and Dev. 5, 97–104.
Xue, D. et al. (1996). Genes & Dev. 10, 1073–1083.
Yang, J., et al. (1997). Science, 275, 1129–1132.
Yokoyama, C., et al. (1993). Cell 75, 187–197.
Yuan, J-Y., et al. (1993). Cell 75, 641–652.
Zamzami, N., (1996). J. Exp. Med. 183, 1523–1544.

EXAMPLE

Protocol for high throughput DFF45-DFF40 binding assay.

A. Reagents

Neutralite Avidin: 20 μg/ml in PBS.

Blocking buffer: 5% BSA, 0.5% Tween 20 in PBS; 1 hour at room temperature.

Assay Buffer: 100 mM KCl, 20 mM HEPES pH 7.6, 1 mM MgCl$_2$, 1% glycerol, 0.5% NP-40, 50 mM β-mercaptoethanol, 1 mg/ml BSA, cocktail of protease inhibitors.

$^{33}$P DFF-45 polypeptide 10×stock: $10^{-8}$–$10^{31\ 6}$ M "cold" DFF-45 supplemented with 200,000–250,000 cpm of labeled DFF-45 (Beckman counter). Place in the 4° C. microfridge during screening.

Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVO$_3$ (Sigma #S-6508) in 10 ml of PBS.

DFF-40: $10^{-7}$–$10^{-5}$ M biotinylated DFF-40 in PBS.

B. Preparation of Assay Plates

Coat with 120 µl of stock N-Avidin per well overnight at 4° C.

Wash 2 times with 200 µl PBS.

Block with 150 µl of blocking buffer.

Wash 2 times with 200 µl PBS.

C. Assay

Add 40 µl assay buffer/well.

add 10 µl compound or extract.

Add 10 µl $^{33}$P-DFF-45 (20–25,000 cpm/0.1–10 pmoles/well=$10^{-9}$–$10^{-7}$ M final conc).

Shake at 25° C. for 15 minutes.

Incubate additional 45 minutes at 25° C.

Add 40 µM biotinylated DFF-40 (0.1–10 pmoles/40 µl in assay buffer)

Incubate 1 hour at room temperature.

Stop the reaction by washing 4 times with 200 µM PBS.

Add 150 µM scintillation cocktail.

Count in Topcount.

D. Controls for All Assays (Located on Each Plate)

a. Non-specific binding b. Soluble (non-biotinylated DFF-40) at 80% inhibition.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated, recombinant expression vector which encodes and expresses a polypeptide comprising at least 10 consecutive amino acid residues of SEQ ID NO:2, wherein said consecutive amino acid residues elicit an antibody which specifically binds a protein consisting of SEQ ID NO:2.

2. An isolated recombinant expression vector according to claim 1, wherein the sequence encodes at least 14 consecutive amino acid residues of SEQ ID NO:2.

3. An isolated, recombinant expression vector which encodes and expresses a polypeptide comprising SEQ ID NO:2.

4. A cell comprising an expression vector according to claim 1.

5. A cell comprising an expression vector according to claim 2.

6. A cell comprising an expression vector according to claim 3.

7. A method of making a polypeptide, comprising steps: introducing an expression vector according to claim 1 into a host cell or cellular extract, incubating said host cell or extract under conditions whereby said polypeptide is expressed as a translation product of said expression vector, and isolating said polypeptide.

8. A method of making a polypeptide, comprising steps: introducing an expression vector according to claim 2 to a host cell or cellular extract, incubating said host cell or extract under conditions whereby said polypeptide is expressed as a translation product of said expression vector, and isolating said polypeptide.

9. A method of making a polypeptide, comprising steps: introducing an expression vector according to claim 3 into a host cell or cellular extract, incubating said host cell or extract under conditions whereby said polypeptide is expressed as a translation product of said expression vector, and isolating said polypeptide.

10. A polynucleotide consisting of 24 consecutive nucleotides of SEQ ID NO:1.

11. A polynucleotide consisting of 36 consecutive nucleotides of SEQ ID NO:1.

12. A polynucleotide consisting of 96 consecutive nucleotides of SEQ ID NO:1.

13. An isolated, recombinant polynucleotide comprising a sequence selected from the group consisting of: nucleotides 113–463, nucleotides 464–784, and nucleotides 785–1105 of SEQ ID NO:1.

14. An isolated, recombinant polynucleotide according to claim 13, wherein the sequence comprises SEQ ID NO:1.

15. An isolated, recombinant expression vector according to claim 1, consisting of a sequence encoding 10, 12 or 14 consecutive amino acid residues of SEQ ID NO:2.

16. An isolated, recombinant expression vector according to claim 1, wherein the sequence encodes a fragment of SEQ ID NO:2 selected from the group consisting of: residues 1–117, residues 118–224 and residues 225–331.

17. A cell comprising an expression vector according to claim 16.

18. A method of making a polypeptide, comprising steps: introducing an expression vector according to claim 16 into a host cell or cellular extract, incubating said host cell or extract under conditions whereby said polypeptide is expressed as a translation product of said expression vector, and isolating said polypeptide.

* * * * *